(12) United States Patent
Patel et al.

(10) Patent No.: US 11,612,674 B2
(45) Date of Patent: *Mar. 28, 2023

(54) ABSORBENT ARTICLES HAVING POCKETS AND RELATED METHODS THEREFOR

(71) Applicant: KPR U.S., LLC, Mansfield, MA (US)

(72) Inventors: Harish A. Patel, Norfolk, MA (US); Richard E. Gahan, Wrentham, MA (US); Vishal Narvekar, Mansfield, MA (US)

(73) Assignee: KPR U.S., LLC, Mansfield, MA (US)

( * ) Notice: Subject to any disclaimer, the term of this patent is extended or adjusted under 35 U.S.C. 154(b) by 736 days.

This patent is subject to a terminal disclaimer.

(21) Appl. No.: 16/502,772

(22) Filed: Jul. 3, 2019

(65) Prior Publication Data

US 2019/0321508 A1 Oct. 24, 2019

Related U.S. Application Data

(63) Continuation of application No. 14/040,761, filed on Sep. 30, 2013, now Pat. No. 10,369,246.
(Continued)

(51) Int. Cl.
*A61L 15/20* (2006.01)
*A61F 13/539* (2006.01)
(Continued)

(52) U.S. Cl.
CPC ............ *A61L 15/24* (2013.01); *A61F 13/534* (2013.01); *A61F 13/535* (2013.01);
(Continued)

(58) Field of Classification Search
CPC .... A61F 13/534; A61F 13/535; A61F 13/539; A61F 2013/530562
See application file for complete search history.

(56) References Cited

U.S. PATENT DOCUMENTS 3,085,309 A * 4/1963 Olson .................. A61F 13/534
428/95
3,816,231 A 6/1974 Marshall
(Continued)

FOREIGN PATENT DOCUMENTS

CA 2906518 A1 9/2014
CN 1244881 A 2/2000
(Continued)

OTHER PUBLICATIONS

Superabsorbent polymers and rewet performance of the internal layers of absorbent disposable products by Kevin T. Hodgson, Aug. 1991, pp. 205-212.
(Continued)

*Primary Examiner* — Michele M Kidwell
(74) *Attorney, Agent, or Firm* — ArentFox Schiff LLP

(57) ABSTRACT

The present disclosure provides articles having an absorbent core with a plurality of segmented volumes defined by a network of filaments, with an absorbent material therein. Suitable articles which may be formed with this absorbent core include, for example, diapers such as infant diapers, juvenile diapers and training pants, feminine hygiene products such as menstrual pads, adult incontinence products such as adult briefs, protective underwear, pads and bladder control pads, pet training pads, and other disposable products utilized to absorb fluids.

25 Claims, 5 Drawing Sheets

Related U.S. Application Data

(60) Provisional application No. 61/835,355, filed on Jun. 14, 2013.

(51) Int. Cl.
    *A61F 13/534*      (2006.01)
    *A61F 13/535*      (2006.01)
    *A61F 13/53*      (2006.01)
    *A61L 15/24*      (2006.01)

(52) U.S. Cl.
    CPC ............ *A61F 13/539* (2013.01); *A61L 15/20* (2013.01); *A61F 2013/530153* (2013.01); *A61F 2013/530562* (2013.01); *Y10T 156/10* (2015.01)

(56) References Cited

U.S. PATENT DOCUMENTS

| | | |
|---|---|---|
| 4,055,180 A | 10/1977 | Karami |
| 4,235,237 A | 11/1980 | Butterworth et al. |
| 4,360,021 A | 11/1982 | Stima |
| 4,573,986 A | 3/1986 | Minetola et al. |
| 4,676,784 A | 6/1987 | Erdman et al. |
| 4,695,278 A | 9/1987 | Lawson |
| 4,710,185 A | 12/1987 | Sneyd, Jr. et al. |
| 4,795,454 A | 1/1989 | Dragoo et al. |
| 5,118,376 A | 6/1992 | Pigneul et al. |
| 5,175,046 A | 12/1992 | Nguyen |
| 5,271,987 A | 12/1993 | Iskra |
| 5,360,420 A | 11/1994 | Cook et al. |
| 5,411,497 A | 5/1995 | Tanzer et al. |
| 5,478,335 A | 12/1995 | Colbert |
| 5,514,120 A | 5/1996 | Johnston et al. |
| 5,531,729 A | 7/1996 | Coles et al. |
| 5,562,645 A | 10/1996 | Tanzer et al. |
| 5,601,542 A | 2/1997 | Melius et al. |
| 5,603,707 A | 2/1997 | Trombetta et al. |
| 5,643,238 A | 7/1997 | Baker |
| 5,713,881 A | 2/1998 | Rezai et al. |
| 5,728,446 A | 3/1998 | Johnston et al. |
| 5,788,684 A | 8/1998 | Abuto et al. |
| 5,938,650 A | 8/1999 | Baer et al. |
| 6,068,620 A | 5/2000 | Chmielewski |
| 6,120,485 A | 9/2000 | Gustafsson et al. |
| 6,129,717 A | 10/2000 | Fujioka et al. |
| 6,140,550 A | 10/2000 | Beihoffer et al. |
| 6,204,207 B1 | 3/2001 | Cederblad et al. |
| 6,251,479 B1 | 6/2001 | Groitzsch et al. |
| 6,290,686 B1 | 9/2001 | Tanzer |
| 6,362,389 B1 | 3/2002 | McDowall et al. |
| 6,383,960 B1 | 5/2002 | Everett et al. |
| 6,387,471 B1 | 5/2002 | Taylor et al. |
| 6,403,857 B1 | 6/2002 | Gross et al. |
| 6,437,214 B1 | 8/2002 | Everett et al. |
| 6,575,952 B2 | 6/2003 | Kirk et al. |
| 6,590,138 B2 | 7/2003 | Onishi |
| 6,610,900 B1 | 8/2003 | Tanzer |
| 6,649,810 B1 | 11/2003 | Minato et al. |
| 6,692,606 B1 | 2/2004 | Cederblad et al. |
| 6,790,798 B1 | 9/2004 | Suzuki et al. |
| 6,794,557 B1 | 9/2004 | Klemp et al. |
| 6,960,197 B1 | 11/2005 | Gustafsson et al. |
| 7,005,558 B1 | 2/2006 | Johansson et al. |
| 7,344,522 B2 | 3/2008 | Suzuki et al. |
| 7,345,004 B2 * | 3/2008 | Zenker .............. A61F 13/15658 442/13 |
| 7,355,091 B2 | 4/2008 | Kellenberger et al. |
| 7,405,341 B2 | 7/2008 | Beruda et al. |
| 7,594,906 B2 | 9/2009 | Bean et al. |
| 7,642,207 B2 | 1/2010 | Roberts et al. |
| 7,662,460 B2 | 2/2010 | Herfert et al. |
| 7,687,680 B2 | 3/2010 | Fell et al. |
| 7,744,576 B2 | 6/2010 | Busam et al. |
| 7,745,687 B2 | 6/2010 | Heyn et al. |
| 7,759,540 B2 | 7/2010 | Litvay et al. |
| 7,838,721 B2 | 11/2010 | Chen |
| 7,851,669 B2 | 12/2010 | Nakagawa et al. |
| 7,855,314 B2 | 12/2010 | Hanao et al. |
| 7,867,210 B2 | 1/2011 | Mori et al. |
| 7,884,259 B2 | 2/2011 | Hanao et al. |
| 7,935,860 B2 | 5/2011 | Dodge et al. |
| 7,976,523 B2 | 7/2011 | Suzuki et al. |
| 8,187,240 B2 | 5/2012 | Busam et al. |
| 8,283,516 B2 | 10/2012 | Litvay |
| 8,298,205 B2 | 10/2012 | Norrby et al. |
| 8,324,446 B2 | 12/2012 | Wang et al. |
| 8,329,292 B2 | 12/2012 | Toonen et al. |
| 8,329,978 B2 | 12/2012 | Uchimoto et al. |
| 8,387,497 B2 | 3/2013 | Raidel et al. |
| 8,633,347 B2 | 1/2014 | Bianco et al. |
| 8,710,293 B2 | 4/2014 | Zhang et al. |
| 8,785,715 B2 | 7/2014 | Wright et al. |
| 8,785,716 B2 | 7/2014 | Schafer et al. |
| 8,927,803 B2 | 1/2015 | Sakai et al. |
| 8,969,652 B2 | 3/2015 | Bewick-Sonntag et al. |
| 9,066,835 B2 | 6/2015 | Okawa et al. |
| 9,072,634 B2 | 7/2015 | Hundorf et al. |
| 9,072,635 B2 | 7/2015 | Katsuragawa et al. |
| 9,072,807 B2 | 7/2015 | Katsuragawa et al. |
| 9,084,700 B2 | 7/2015 | Litvay |
| 9,125,758 B2 | 9/2015 | Skreosen |
| 9,440,001 B2 | 9/2016 | Kettlewell et al. |
| 9,572,728 B2 | 2/2017 | Ashton et al. |
| 9,603,754 B2 | 3/2017 | Tsang et al. |
| 9,675,501 B2 | 6/2017 | Ong et al. |
| 9,687,394 B2 | 6/2017 | Varona et al. |
| 9,693,911 B2 | 7/2017 | Sheldon et al. |
| 9,707,135 B2 | 7/2017 | Sheldon et al. |
| 9,713,556 B2 | 7/2017 | Arizti et al. |
| 9,750,651 B2 | 9/2017 | Bianchi et al. |
| 9,757,284 B2 | 9/2017 | Tsang et al. |
| 9,789,012 B2 | 10/2017 | Chmielewski et al. |
| 9,789,014 B2 | 10/2017 | Wright et al. |
| 10,052,242 B2 | 8/2018 | Bianchi et al. |
| 2001/0041876 A1 | 11/2001 | Creagan et al. |
| 2003/0012928 A1 | 1/2003 | Malowaniec et al. |
| 2003/0114813 A1 | 6/2003 | Dodge et al. |
| 2003/0114814 A1 | 6/2003 | Baker et al. |
| 2003/0129915 A1 | 7/2003 | Harriz |
| 2003/0135177 A1 | 7/2003 | Baker |
| 2003/0149413 A1 | 8/2003 | Mehawej |
| 2003/0181882 A1 | 9/2003 | Toyoshima et al. |
| 2003/0187413 A1 | 10/2003 | Fell |
| 2003/0195485 A1 | 10/2003 | Rangachari et al. |
| 2003/0225384 A1 | 12/2003 | Zenker et al. |
| 2004/0024375 A1 | 2/2004 | Litvay |
| 2004/0054342 A1 | 3/2004 | Newbill et al. |
| 2004/0087923 A1 | 5/2004 | Cole |
| 2005/0058810 A1 | 3/2005 | Dodge et al. |
| 2005/0101929 A1 | 5/2005 | Waksmundzki et al. |
| 2005/0107759 A1 | 5/2005 | Waksmundzki et al. |
| 2005/0130540 A1 | 6/2005 | Crane |
| 2005/0165376 A1 | 7/2005 | Buchholz et al. |
| 2006/0020250 A1 | 1/2006 | Chester et al. |
| 2006/0040579 A1 | 2/2006 | Sheldon et al. |
| 2006/0069367 A1 | 3/2006 | Waksmundzki et al. |
| 2006/0167424 A1 | 7/2006 | Chang et al. |
| 2006/0173432 A1 | 8/2006 | Laumer et al. |
| 2007/0031637 A1 | 2/2007 | Anderson |
| 2007/0156107 A1 | 7/2007 | Kimura et al. |
| 2007/0191798 A1 | 8/2007 | Glaug et al. |
| 2008/0058747 A1 | 3/2008 | Singh et al. |
| 2009/0076473 A1 | 3/2009 | Kasai et al. |
| 2009/0187155 A1 | 7/2009 | Razavi |
| 2012/0316529 A1 | 12/2012 | Kreuzer et al. |
| 2013/0018348 A1 | 1/2013 | Carlucci et al. |
| 2013/0025795 A1 | 1/2013 | Ukegawa et al. |
| 2013/0079741 A1 | 3/2013 | Nakashita et al. |
| 2014/0081230 A1 | 3/2014 | Litvay |
| 2014/0155853 A1 | 6/2014 | Handziak |
| 2014/0276516 A1 | 9/2014 | Dagher et al. |
| 2014/0315005 A1 | 10/2014 | Strälin |
| 2015/0045756 A1 | 2/2015 | Aright et al. |

(56) References Cited

U.S. PATENT DOCUMENTS

| | | |
|---|---|---|
| 2015/0141947 A1 | 5/2015 | Gahan |
| 2015/0216742 A1 | 8/2015 | Johnson et al. |
| 2015/0320615 A1 | 11/2015 | Bergstrom et al. |
| 2015/0342799 A1 | 12/2015 | Michiels et al. |
| 2015/0342802 A1 | 12/2015 | Caputi et al. |
| 2016/0030258 A1 | 2/2016 | Wei et al. |
| 2016/0051420 A1 | 2/2016 | Schroer, Jr. |
| 2016/0136009 A1 | 5/2016 | Weisman et al. |
| 2016/0143247 A1 | 5/2016 | Szypka |
| 2016/0220427 A1 | 8/2016 | Ducker |
| 2016/0228304 A1 | 8/2016 | Orechva |
| 2017/0102306 A1 | 4/2017 | Dagher et al. |
| 2017/0165131 A1 | 6/2017 | Varona et al. |
| 2017/0209616 A1 | 7/2017 | Turner |
| 2017/0281427 A1 | 10/2017 | Sheldon et al. |
| 2018/0001591 A1 | 1/2018 | Dutkiewicz et al. |
| 2018/0008488 A1 | 1/2018 | Sheldon et al. |
| 2018/0098889 A1 | 4/2018 | Hardie et al. |
| 2018/0140481 A1 | 5/2018 | Sheldon et al. |

FOREIGN PATENT DOCUMENTS

| | | |
|---|---|---|
| CN | 1833623 A | 9/2006 |
| CN | 101426461 A | 5/2009 |
| EP | 0174152 A1 | 3/1986 |
| EP | 0425270 A2 | 5/1991 |
| EP | 0430443 A1 | 6/1991 |
| EP | 0558889 B1 | 3/1996 |
| EP | 0555346 B1 | 5/1996 |
| EP | 0829245 A2 | 3/1998 |
| EP | 0947549 B1 | 11/2011 |
| EP | 2952166 A1 | 12/2015 |
| EP | 2968032 A2 | 1/2016 |
| EP | 2992864 A1 | 3/2016 |
| EP | 2901991 B1 | 4/2016 |
| EP | 2901992 B1 | 12/2016 |
| EP | 3251647 A1 | 12/2017 |
| JP | 2016511133 A | 4/2016 |
| MX | 2015013038 A | 11/2016 |
| WO | 9510995 A1 | 4/1995 |
| WO | 9942067 A1 | 8/1999 |
| WO | 2004110325 A1 | 12/2004 |
| WO | 2014151544 A2 | 9/2014 |
| WO | 2017138962 A1 | 8/2017 |

OTHER PUBLICATIONS

Superabsorbent Polymers and Superabsorbent Polymer Composites by Suda Kiatkamjornwong, ScienceAsia 33 Supplement 1 (2007), pp. 39-43.

Superabsorbent Polymers by Mark Ellioti, pp. 1-13.

Water Saturated Super-Absorbent Polymers Used in High Strength Concrete by Sven Monnig, Otto-Graf-Journal vol. 16, 2005, pp. 193-202.

* cited by examiner

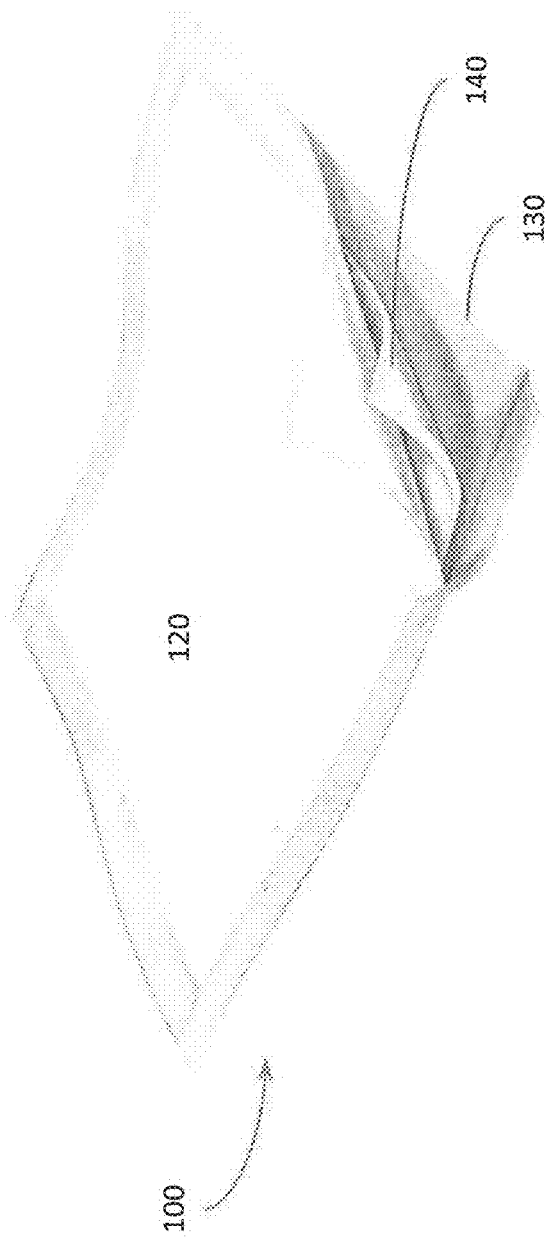
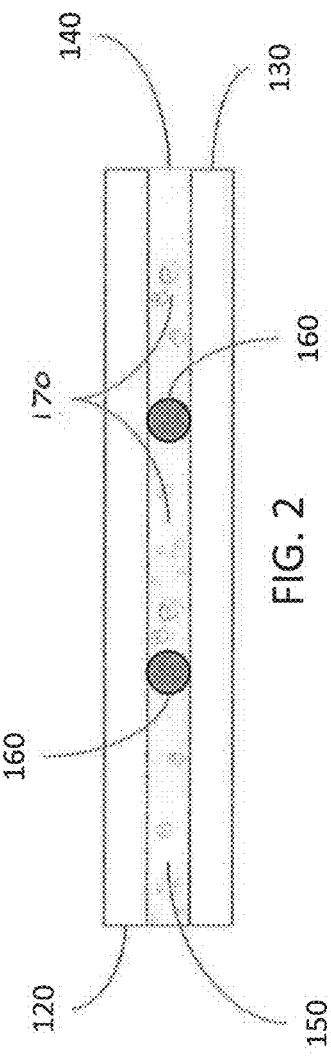

ABSORBENT ARTICLES HAVING POCKETS AND RELATED METHODS THEREFOR

CROSS REFERENCE TO RELATED APPLICATIONS

This application is a continuation of U.S. patent application Ser. No. 14/040,761, filed Sep. 30, 2013, which claims priority to U.S. Provisional Application No. 61/835,355, filed Jun. 14, 2013, the entirety of both of which is hereby incorporated by reference herein.

BACKGROUND

Field

The present disclosure pertains to absorbent articles having an absorbent structure with a plurality of segmented volumes containing or confining absorbent material therewithin. In embodiments, the present disclosure pertains to absorbent articles, such as but not limited to, diapers, protective undergarments, and absorbent pads, having absorbent material segmented into pockets.

Description of Related Art

Absorbent articles often have a first liquid permeable layer disposed proximate or even adjacent a skin surface, an outer impermeable layer, and an absorbent core disposed between the first liquid permeable layer and the outer permeable layer.

The absorbent core can include one or more absorbent materials, including a mixture of superabsorbent polymer and fluff pulp. Some products have an embossed core that defines diamond-shaped pockets including a mixture of fluff pulp material and superabsorbent polymer particles. The embossing process, however, relies of hydrogen bonding phenomena to create the defined embossing lines.

SUMMARY

One or more aspects of the present disclosure can be directed to an absorbent article including a fluid permeable inner layer; an impermeable outer layer; and an absorbent layer disposed between the permeable inner layer and the impermeable outer layer, the absorbent layer including superabsorbent material in a plurality of segmented volumes, referred to, in embodiments, as pockets, at least partially defined by a net having filaments thereof secured to the permeable inner layer.

The absorbent layer can further include fluff pulp in at least one of the plurality of pockets. The net can be a polymeric material having a melting point less than a melting point of a material forming the permeable inner layer. The polymeric material of the net can be a polymer such as a polyethylene, polypropylene, polyester, and/or polyamide. In embodiments, the polymeric material of the net is a polymer selected from the group consisting essentially of polyethylene, polypropylene, polyester, and polyamide. In other embodiments, the polymeric material of the net is a polymer selected from the group consisting of polyethylene, polypropylene, polyester, and polyamide.

Each of the plurality of pockets is at least partially defined by the net adhesively secured to the permeable inner layer and to the impermeable outer layer. In some embodiments of the disclosure, each of the plurality of pockets can be substantially about the same size; however, other variants thereof may involve embodiments wherein the pockets are of differing size.

The superabsorbent material can include starch-graft polymers and cross-linked polyacrylate polymers. The superabsorbent material can be a polymer such as a polyacrylamide, polyethylene oxide, polyvinyl alcohol, polysuccinimide, and hydrolyzed polyacrylonitrile. In embodiments, the superabsorbent material is a polymer selected from the group consisting essentially of polyacrylamide, polyethylene oxide, polyvinyl alcohol, polysuccinimide, and hydrolyzed polyacrylonitrile. In other embodiments, the superabsorbent material is a polymer selected from the group consisting of polyacrylamide, polyethylene oxide, polyvinyl alcohol, polysuccinimide, and hydrolyzed polyacrylonitrile.

In other embodiments relative to one or more aspects of the disclosure, the filaments can be formed of cotton with a thread count per square inch in a range of from about 2×2 to about 8×8, wherein at least a portion of the filaments are secured to the permeable inner layer and to the impermeable outer layer with an adhesive. In still further embodiments of the disclosure, at least a portion of the pockets is sized to have at least one dimension from about 0.125 inch to about 1 inch.

In yet further embodiments of the disclosure, at least a portion of the plurality of pockets have a first area and at least a portion of the plurality of pockets have a second area, with the first area greater than the second area, and wherein at least a portion of the plurality of pockets with the first area is disposed at a peripheral zone of the absorbent article. In further embodiments of the disclosure, at least a portion of the filaments can be formed of an elastomeric material with a diameter from about 250 microns to about 500 microns.

One or more aspects of the disclosure can be directed to a method of preparing an absorbent article having a permeable inner layer and an impermeable outer layer having a network of filaments, the method including disposing superabsorbent material between the network of filaments and securing at least a portion of the network of filaments to at least one of the fluid permeable inner layer and the impermeable outer layer. Securing the at least a portion of the network of filaments can involve melting at least a portion of the filaments. In other cases, securing the at least a portion of the network of filament defines an absorbent layer having a plurality of pockets, and the method further includes disposing fluff pulp into at least a portion of the plurality of pockets. In still further cases, securing the at least a portion of the network of filaments includes adhesively securing at least a portion of the network of filaments to the impermeable outer layer. In yet further cases, adhesively securing the at least a portion of the network of filaments to the impermeable outer layer includes applying, on at least one of the impermeable outer layer and the network of filaments, an adhesive including at least one hydrophilic polymer.

One or more aspects of the disclosure can be directed to a protective undergarment comprising a top sheet; a bottom sheet; and an absorbent core disposed between the top sheet and the bottom sheet, the absorbent core comprising a superabsorbent material in a plurality of pockets at least partially defined by a net having filaments thereof secured to the top sheet or bottom sheet.

One or more aspects of the disclosure can be directed to a diaper comprising a top sheet; a bottom sheet; and an absorbent core disposed between the top sheet and the bottom sheet, the absorbent core comprising a superabsorbent material in a plurality of pockets at least partially defined by a net having filaments thereof secured to the top sheet or bottom sheet.

DESCRIPTION OF THE DRAWINGS

The features and advantages of the disclosure will become apparent with regard to the following description, claims and accompanying figures where:

FIG. 1 is a schematic illustration showing an absorbent article having a liquid permeable layer, an absorbent layer including pocketed regions, and an outer impermeable layer, in accordance with one or more aspects of the present disclosure;

FIG. 2 is a schematic illustration showing a cross-section of an absorbent article, in accordance with one or more aspects of the present disclosure;

DESCRIPTION

The following description of the presently disclosed absorbent articles can include a substrate upon and within which fluid discharge, e.g., liquid insult, may be applied and absorbed. For illustrative purposes, the absorbent article will be discussed in terms of a patient care underpad and diaper; however, the presently disclosed absorbent articles may be any absorbent product such as, for example, training pants, feminine hygiene products such as menstrual pads, adult incontinence products such as adult briefs, protective underwear, pads and bladder control pads, pet training pads, and other disposable products utilized to absorb fluids.

Absorbent articles with certain advantageous features often include a multi-layer arrangement with a fluid permeable top sheet for engaging the body surface, a fluid impermeable back sheet for preventing fluid leakage through the article, and an absorbent core disposed therebetween. One or more aspects of the presently disclosed articles and related methods therefor involve a preformed net or network of filaments to facilitate pocket formation. The net can advantageously provide pockets of any desired or predetermined shape such as, but not limited to, square, rectangular, hexagonal, and diamond shaped pockets, or combinations thereof in the absorbent article. Further, the use of the net can also advantageously provide absorbent articles including pockets of varied dimensions or sizes.

The absorbent core can be formed on a conventional pocket former and the net can be laid thereon. If the net includes an elastic material, the net can be stretched so that fluff pulp material and superabsorbent material pillows between the net filaments. The net can be applied on the top or the bottom of the core and thermally melted into the absorbent mixture, which can trap and inhibit the absorbent mixture from moving to other regions of the absorbent core or the absorbent article. Trapping or confining the absorbent material advantageously allows retention of the shape of the absorbent core both before and after liquid insult. Thus, it is believed, immobilizing the absorbent materials in predefined regions allows predictable absorption performance characteristics.

Figure 3:
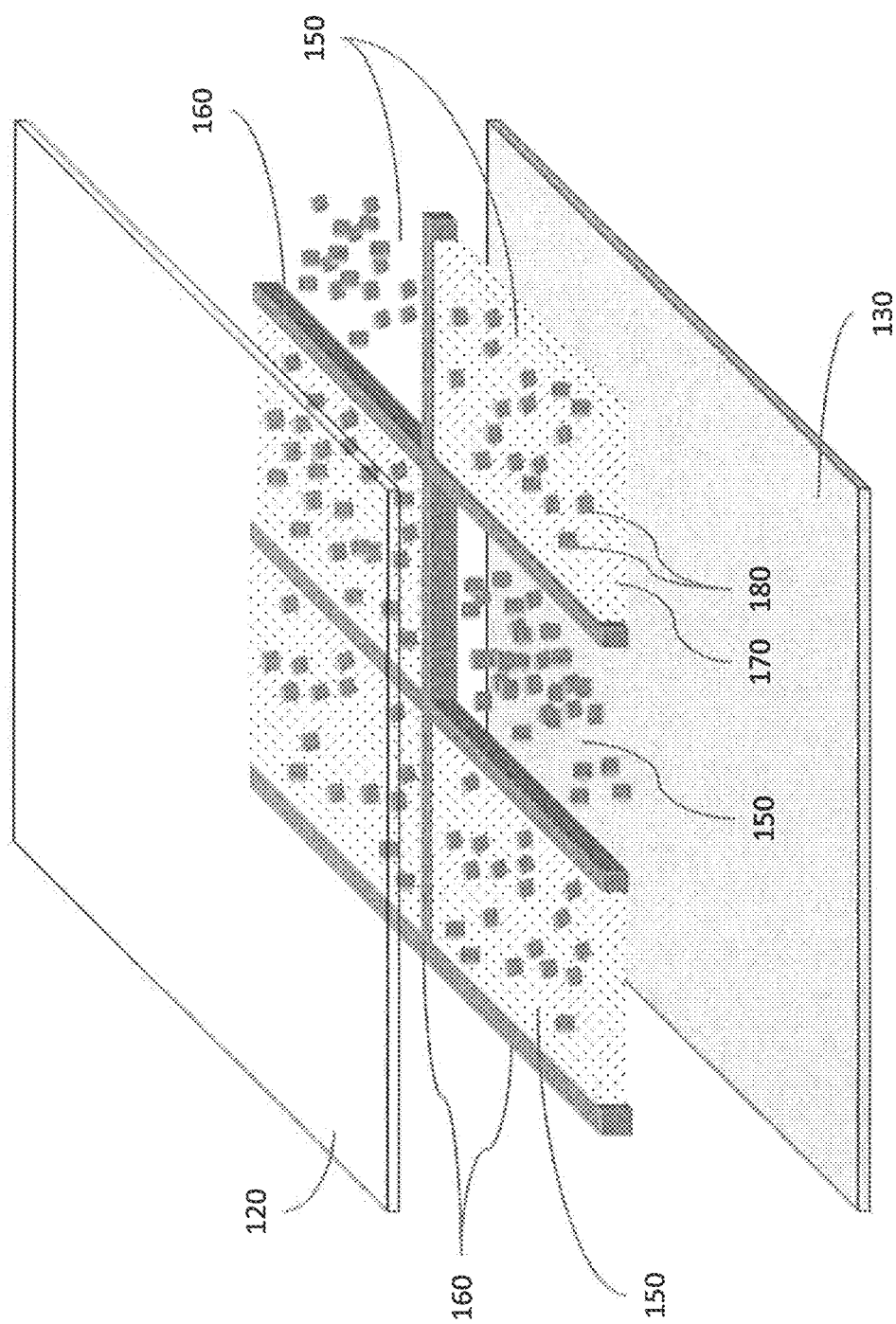
FIG. 3 is a schematic illustration showing a portion of an absorbent article, in accordance with one or more aspects of the present disclosure.

Referring to FIGS. 1-3, an exemplary absorbent article 100 in accordance with one or more aspects of the present disclosure can be an absorbent pad having a first layer or top sheet, often a liquid permeable layer 120 and a second layer or bottom sheet, often an impermeable layer 130. The absorbent article 100 can further include an absorbent core 140, with one or more absorbent layers, disposed between the first layer 120 and the second layer 130. In use, the absorbent article is placed against a user such that it is positioned to receive fluid discharge from the user. When the absorbent article receives fluid discharge, such as an insult of fluid from the user, a majority of the fluid passes through the top sheet 120 and is absorbed by the absorbent core 140. The underpad is often discarded after one insult.

Top sheet 120 can be a woven or nonwoven fabric including polymeric fibers. In some cases, top sheet 120 can be formed of one or more bicomponent polymeric fibers. For example, top sheet 120 can be a fabric with first bicomponent fibers woven with second bicomponent fibers. Top sheet 120 is often a fluid pervious layer for permitting liquid, e.g., menses or urine, to penetrate readily through its thickness. Top sheet 120 may be compliant and/or soft to the touch so that it does not irritate skin. In some advantageous configurations, the sheet 120 may be formed of woven or non-woven materials, e.g., a non-woven web of fibers; polymeric materials such as thermoplastic films having apertures, plastic films having apertures, and hydro-formed thermoplastic films; porous foams; reticulated foams; reticulated thermoplastic films; and thermoplastic scrims. Fibers that may be utilized to construct woven and non-woven materials include, for example, natural fibers, e.g., wood or cotton fibers, synthetic fibers, e.g., polymeric fibers such as polyester, polypropylene, or polyethylene fibers, and combinations of natural and synthetic fibers.

In embodiments, fibers may be fixedly secured by adhesives, such as hot melt, or by other techniques, including, for example and without limitation, ultrasonic bonding, heat pressure sealing, and hot air knife bonding.

In embodiments in which the top sheet 120 is a nonwoven web, the web may be spun-bonded, carded, wet-laid, melt-blown, or hydro-entangled. In accordance with further embodiments of the disclosure, at least a portion of the liquid pervious top sheet can be formed of a nonwoven fibrous layer of polyolefinic fibers. The fibers can be multicomponent fibers. At least a portion of the fibers of at least a portion of the top sheet 120 can be bicomponent fibers having a first component that has a first fusion point and a second component that has a second fusion point that is less than the first fusion point. In accordance with still further aspects of the disclosure, at least a portion of the top sheet can include thermobondable polymeric bicomponent fibers including a high-melting point core and a low melting point sheath substantially surrounding the core. The top sheet 120 can include at least about 50% by weight of bicomponent fibers. Thus, for example, the top sheet can include monolithic fibers formed of a polyolefin which, in some cases, can be the same polyolefin as the core. In other embodiments, the top sheet 120 includes bicomponent fibers. In still other embodiments, the top sheet 120 consists essentially of bicomponent fibers. In yet other embodiments, top sheet 120 consists of bicomponent fibers.

The top sheet 120 can thus include bicomponent fibers having a core of a first polyolefin and a sheath around the core of a second polyolefin. The top sheet 120 can also consist essentially of bicomponent fibers having a core of a first polyolefin and a sheath around the core of a second polyolefin. In other embodiments, the top sheet 120 consists of bicomponent fibers having a core of a first polyolefin and a sheath around the core of a second polyolefin.

In some configurations, the top sheet 120 can include a plurality of layers. For example, the top sheet 120 can include a first layer, as the body side layer, including bicomponent fibers and a second layer, distal to the body side layer, including monocomponent fibers. In some configurations of the top sheet, the second layer can include spun bond monocomponent fibers of polyolefin, which may be a polyethylene, and can be the same polyethylene of the sheath of the bicomponent fibers of the first layer. In other embodiments, the top sheet 120 includes a first layer, preferably as the body side layer, consisting of or consisting essentially of bicomponent fibers, and a second layer, typically a distal second layer, including or consisting of monocomponent fibers. In some particular configurations of the top sheet, the second layer can consist of spun bond monocomponent fibers of polyolefin, in some cases a polyethylene, and can be the same polyethylene of the sheath of the bicomponent fibers of the first layer.

In other embodiments, the first polyolefin can be a polypropylene and the second polyolefin can be polyethylene. In other configurations, the first polyolefin can be a high-density polyethylene and the second polyolefin can be low-density polyethylene. For example, the sheath can include a linear low-density polyethylene having a density of less than or about 0.95 $g/cm^3$. The core can include a high-density polyethylene having a density of greater than 0.95 $g/cm^3$.

The bottom sheet 130 can be a fluid impervious layer for preventing liquid absorbed and contained in the absorbent core 140 from wetting articles which contact the underpad, such as, but not limited to, undergarments, pants, pajamas, and bed sheets. The bottom sheet 130 may be: a woven material; a non-woven material; a liquid-impervious fabric; a cellulosic film; a polymeric film such as a thermoplastic film of polyethylene or polypropylene; an impregnated fluid repellent paper; a composite material, e.g., a polylaminate, such as a film-coated non-woven material; or combinations thereof.

The bottom sheet 130, or at least portions thereof, may be embossed or may be matte-finished to provide a cloth-like appearance, and/or colored for ready identification. The bottom sheet 130 may also be breathable to allow at least some vapors to escape or pass from the absorbent core 140, while preventing fluid discharge from passing therethrough.

The absorbent core 140 can include a plurality of pockets 150 at least partially defined therewithin. For example, each of the pockets 150 can be defined by a net or a network of filaments 160 having a defined, predetermined thickness or defined cross-sectional dimensions. Thus, the thickness of the absorbent core 140 may vary to include thicker and/or thinner areas for a desirable performance or characteristic of the absorbent article by utilizing filaments with a predetermined dimension, such as thickness.

The pockets 150 may be sized to have at least one dimension from about 0.125 inch to about 1 inch, in embodiments from about 0.25 inch to about 0.75 inch.

Any one or more of the plurality of pockets 150 can include a fluid absorbing material or composition made from absorbent materials such as, but not limited to, foams; nonwoven composite fabrics; hydrogels; cellulosic fabrics; super absorbent polymers; woven fabrics; tissue; paper; inherently hydrophilic foams, e.g., viscose rayon foam; natural or synthetic foamed polymeric materials, e.g., polyurethane, polyether, or styrene/butadiene rubber foams which have been rendered hydrophilic or readily wettable; comminuted wood pulp; cotton linters and cotton wool of any grade; rayon fibers; cotton staple; bleached or unbleached-creped tissue; and combinations and composites thereof.

The pockets 150 may also contain a fibrous matrix of wood fiber or wood pulp fluff material. In some embodiments, one or more of the pockets 150 includes a fibrous matrix of fluff fibers 170 into or onto which superabsorbent polymer (SAP) particles 180 are dispersed. The amount of wood fiber or wood pulp fluff material in an individual pocket may be from about 0.0 $g/m^2$ to about 100 $g/m^2$, and in some embodiments, from about 5 $g/m^2$ to about 50 $g/m^2$.

Materials for use as the super absorbent polymer particles include starch type, starch-graft polymers, cellulosic, and synthetic types, starch-acrylic acid (salt) graft copolymers, saponified starch-acrylonitrile copolymers, crosslinked sodium carboxymethyl cellulose, acrylic acid (salt) polymers, cross-linked polyacrylate polymers, polyacrylamides, polyethylene oxides, polyvinyl alcohols, polysuccinimides, hydrolyzed polyacrylonitriles, and combinations thereof. As a shape for the super absorbent polymer particles, powder-particle may be desirable, but other shapes can be also used.

The particle diameter of super absorbent polymer particles can be from about 20 μm to about 850 μm, in embodiments from about 110 μm to about 500 μm, in other embodiments about 140 μm to about 350 μm.

Super absorbent polymer particles having an absorption speed of 45 seconds or less can be used. When the absorption speed exceeds 45 seconds, so-called flow back may occur, where body fluids supplied to an absorber flow back outside the absorber.

The SAP particles may be distributed, continuously or discontinuously, through the absorbent core 140 in any of the pockets in a uniform manner or in a manner which creates a distribution gradient of SAP particles therethrough. The gradient can be effected by having the pockets that are proximate a peripheral outer region of absorbent article 100 contain a greater amount of SAP particles relative to pockets that are in the interior or central region of the absorbent article. However, the converse can be a variant embodiment such that pockets that are proximate a peripheral outer region of absorbent article 100 may contain a lesser amount of SAP particles relative to pockets that are in the interior or central region of the absorbent article.

Similarly, fluff material may be distributed through the absorbent core 140 in any of the pockets in a uniform manner or in a manner which creates a distribution gradient of fluff therethrough. For example, an inner zone of the absorbent core 140 can include a higher distribution of fluff fibers than an outer zone. The inner zone can include about 60%, by weight, of the fluff fibers, while the outer zone includes about 40% of the fluff fibers.

The relative amount of SAP can uniformly vary as a function of distance from the central, interior region to create a linear gradient. Other configurations can involve discrete or incremental stepped changes in the relative amount of SAP in the pockets. Further configurations can involve one or more pockets, at any of various regions of the absorbent article, containing only SAP. Still further configurations can involve one or more pockets, at any of various regions of the absorbent article, containing only fluff pulp material.

In embodiments, individual pockets of the absorbent core of the present disclosure may contain SAP in amounts from about 50 g/m² to about 500 g/m², in embodiments from about 300 g/m² to about 380 g/m², in embodiments about 365 g/m².

The ratio of fluff to SAP, by weight, in an individual pocket may be from about 0:1, from 1:80, and in embodiments from about 1 to about 8.

The amount and type of SAP used may also be varied throughout the article to advantageously provide a target performance property or a desired absorption characteristic. Thus, in some cases, a SAP having a faster absorption speed may be used in the central region of the absorbent article, while SAPs having a slower absorption speed may be used at the periphery.

Assembly of the absorbent article can be performed by providing the bottom sheet, securing the net to the bottom sheet, disposing a predetermined amount of any of SAP, fluff pulp, and mixtures thereof in the pockets that are at least partially defined between filaments of the network, and securing the top sheet to at least one of the bottom sheet and the net. The absorbent core including the net can be secured by melting at least a portion, e.g., predetermined portions of the network of filaments, to attach at least one of the top sheet and the bottom sheet thereto. In other embodiments, an adhesive can be used to secure at least a portion, such as predetermined portions of the network of filaments, to attach at least one of the top sheet and the bottom sheet thereto.

The net can be formed of a polymeric material such as polyethylene, polyester, polyamide, biodegradable polymers such as those derived from starch, cellulose and lactic acid, as well as combinations thereof. Other materials for forming the net include, but are not limited to, polyolefins such as polypropylene, blends of polypropylene with ethylene vinyl alcohol, and combinations thereof. In some embodiments, the net is formed of a polymeric material selected from the group consisting of polyethylene, polyester, polyamide, biodegradable polymers such as those derived from starch, cellulose and lactic acid, as well as combinations thereof.

In other embodiments relative to one or more aspects of the present disclosure, the filaments can be formed of cotton with a thread count per square inch of from about 2×2 to about 8×8, wherein at least a portion of the filaments are secured to the permeable inner layer and to the impermeable outer layer with an adhesive.

The net can include bicomponent filaments including, for example, a polymeric material with a first melting temperature or first melting range, and a second polymeric material with a second melting temperature or melting range that is less than the first melting temperature or first melting range. In yet other embodiments, the net can include a hydrophilic material that facilitates transport of aqueous liquids throughout the network. For example, the net can be coated with a surfactant.

Filaments forming the net may have a diameter from about 250 μm to about 500 μm, in embodiments from about 300 μm to about 450 μm.

In accordance with further aspects of the disclosed absorbent articles, the absorbent core can be preformed by laying the net on a drum or pocket and sheets or layers of tissue or cellulosic material can enclose and define the preformed core. The preformed core can then be disposed in any of the various absorbent articles described herein. Adhesives described above for adhering fibers used to construct woven and non-woven materials may also be used to adhere the net to other materials used to form the absorbent core.

As noted above, in embodiments the absorbent core can be used in forming diapers such as infant diapers, juvenile diapers and training pants, feminine hygiene products such as menstrual pads, adult incontinence products such as adult briefs, protective underwear, pads, and bladder control pads, pet training pads, and other disposable products utilized to absorb fluids.

Figure 4:
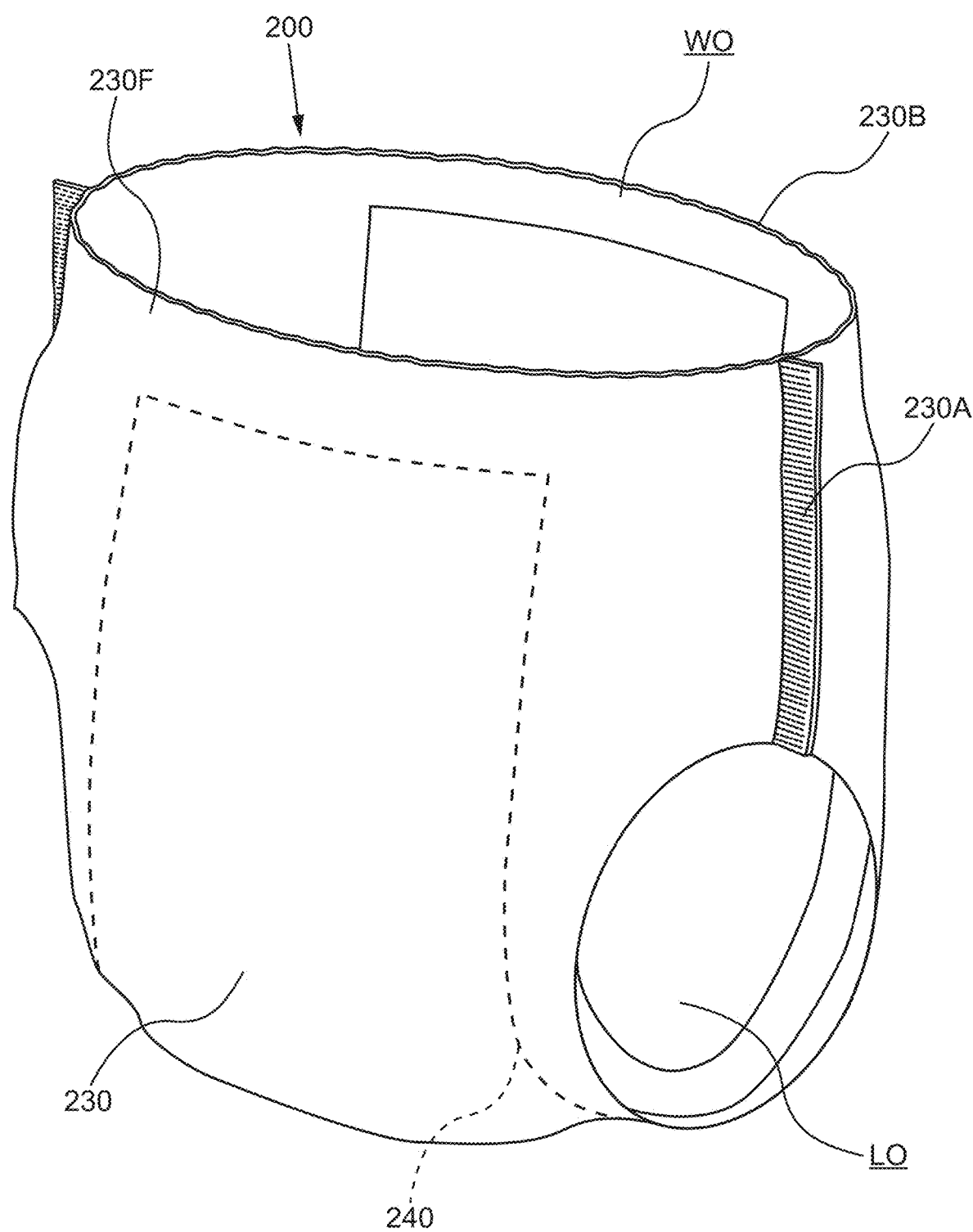
FIG. 4 is a perspective view showing a pant-type diaper which may possess an absorbent article in accordance with one or more aspects of the present disclosure.

FIG. 4 shows an example of a pant-type disposable diaper 200. The pant-type disposable diaper 200 typically has an exterior sheet 230 on or as an outside (backside) surface and an absorbent core 240 on the inside (front side) portion thereof. The absorbent core 240 is, in some cases, fixed to the exterior sheet 230. The absorbent core 240 typically receives and contains body fluids such as urines or soft stools. In some particular cases, any one or more variants or configurations of the absorbent article 140 may comprise a portion or be used as the absorbent core 240 of the diaper 200.

The exterior sheet 230 may be formed of a material suitable for forming bottom sheets. Although the absorbent core 240 may have any shape, it is rectangular in the illustrated embodiment.

The absorbent core 240 may be formed of any material as suitable for forming absorbent cores as disclosed herein. Where the absorbent core is used as a component of a diaper or other protective underwear-type article, the absorbent core may have patterns of pockets and/or differing amounts or concentrations of superabsorbent polymers particles in pockets of the absorbent core. For example, the SAP particles may be continuously or discontinuously distributed through the absorbent core 240 in any of the pockets thereof in a uniform manner or in a manner which creates a distribution gradient of SAP particles therethrough. The gradient can be created by having the pockets that are proximate a peripheral outer region of the diaper 200 contain a greater amount of SAP particles relative to pockets that are in the interior or central region of the diaper 200. However, the converse can be a variant embodiment such that the pockets that are proximate a peripheral outer region of the diaper 200 may contain a lesser amount of SAP particles relative to pockets that are in the interior or central region of the absorbent article. In other cases, diapers and/or protective underwear of the present disclosure may be configured to have zones of superabsorbent sections with an inner zone including a first amount of superabsorbent polymer particles and an outer zone including a second amount of superabsorbent polymer particles. The first amount or distribution of superabsorbent polymer particles may be greater than the second amount or distribution of superabsorbent polymer particles. For example, the inner zone can include about 70%, by weight, of the superabsorbent polymer particles and the outer zone includes about 30% of the superabsorbent polymer particles. This configuration may produce an absorbency gradient, with high levels of absorbency centrally located in areas most likely to be subjected to insult, with lower levels at the periphery to prevent run-off. Other configurations may involve variants that have a converse gradient of amount of SAP particles.

Further, the ratio of SAP to fluff may be maintained and/or altered, in embodiments, by adjusting the size of the pockets, thereby altering the amount of SAP within the pockets, and/or adjusting the concentration of pockets in a given area of the absorbent core or any article possessing the absorbent core.

Similarly, the size of the pockets may differ throughout the absorbent core. Once again, as it may be desirable to have greater absorbency in the center of a diaper or similar protective undergarment, the pockets located therein may be larger, capable of holding larger amounts of superabsorbent polymer therein, with smaller pockets holding smaller amounts of superabsorbent polymer at the periphery. As described above, this configuration will similarly produce an absorbency gradient, with high levels of absorbency centrally located in areas most likely to be subjected to insult, with lower levels at the periphery to prevent run-off.

Figure 5:
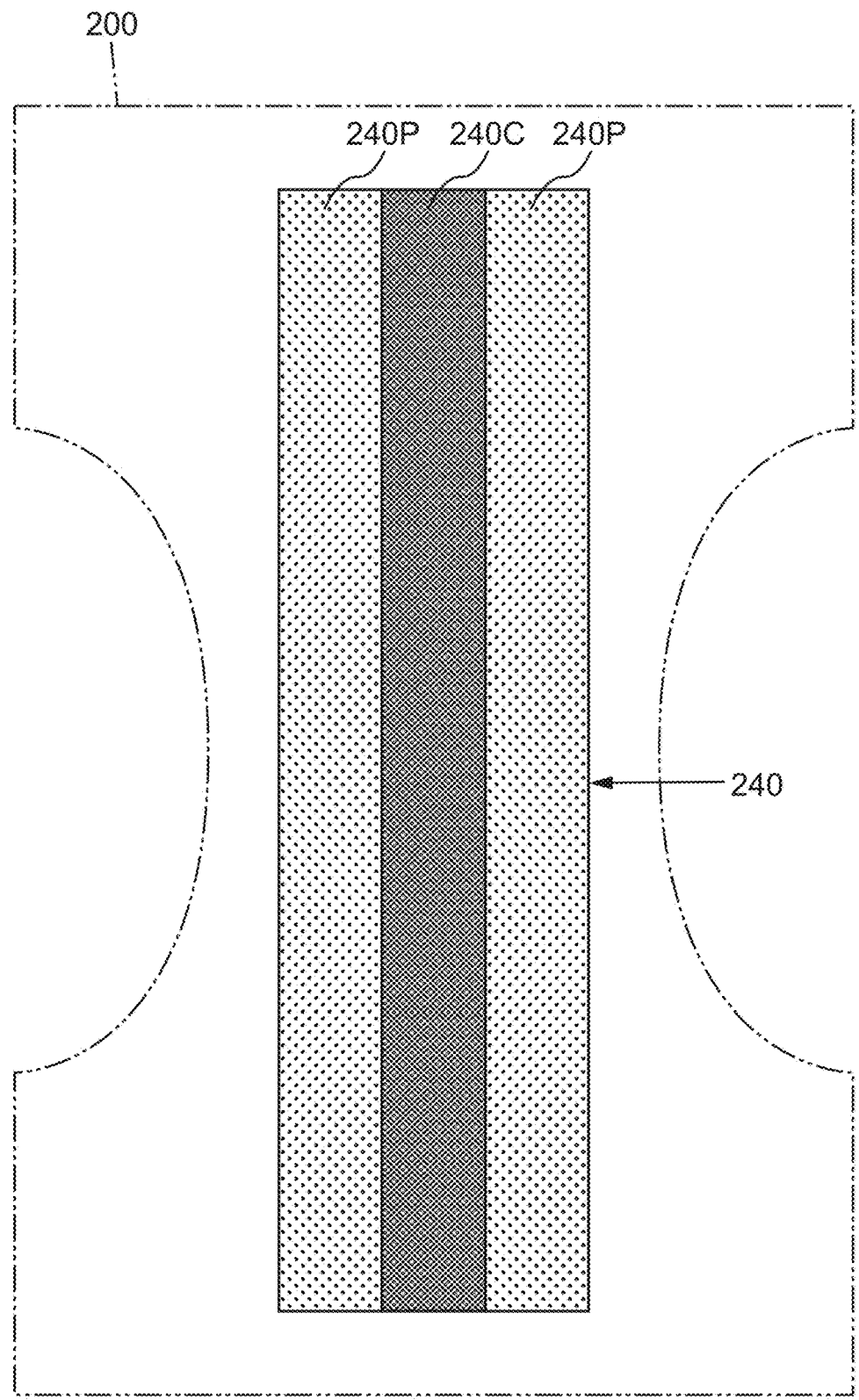
FIG. 5 is a plan view showing a pant-type diaper in an unused state possessing an absorbent article in accordance with one or more aspects of the present disclosure.

FIG. 5 shows an absorbent core 240 in a diaper 200. The absorbent core 240 is exemplarily shown with a central portion 240C having a relatively large amount of super absorbent polymer particles and peripheral portions 240P having a smaller amount of super absorbent polymer particles, relative to the central portion 240C. Thus, some aspects of the disclosure provide absorbent articles having tailored, e.g., non-uniform absorption characteristics, such as the amounts of absorption or capacity at certain portions or zones of the article, as well as tailored absorbency rates at one or more of the same or different zones of the article.

In assembly, the exterior sheet 230 can be folded in front and back, and a front body 230F and a back body 230B of the exterior sheet 230 are joined at junction regions 230A on both sides. In this manner, a pant-type disposable diaper including a waist opening WO and a pair of leg openings LO can be obtained. For an infant diaper, instead of heat sealing, one or more tabs or tapes may be located at junction regions 230A on both sides (not shown) permitting the construction thereof.

Figure 6:
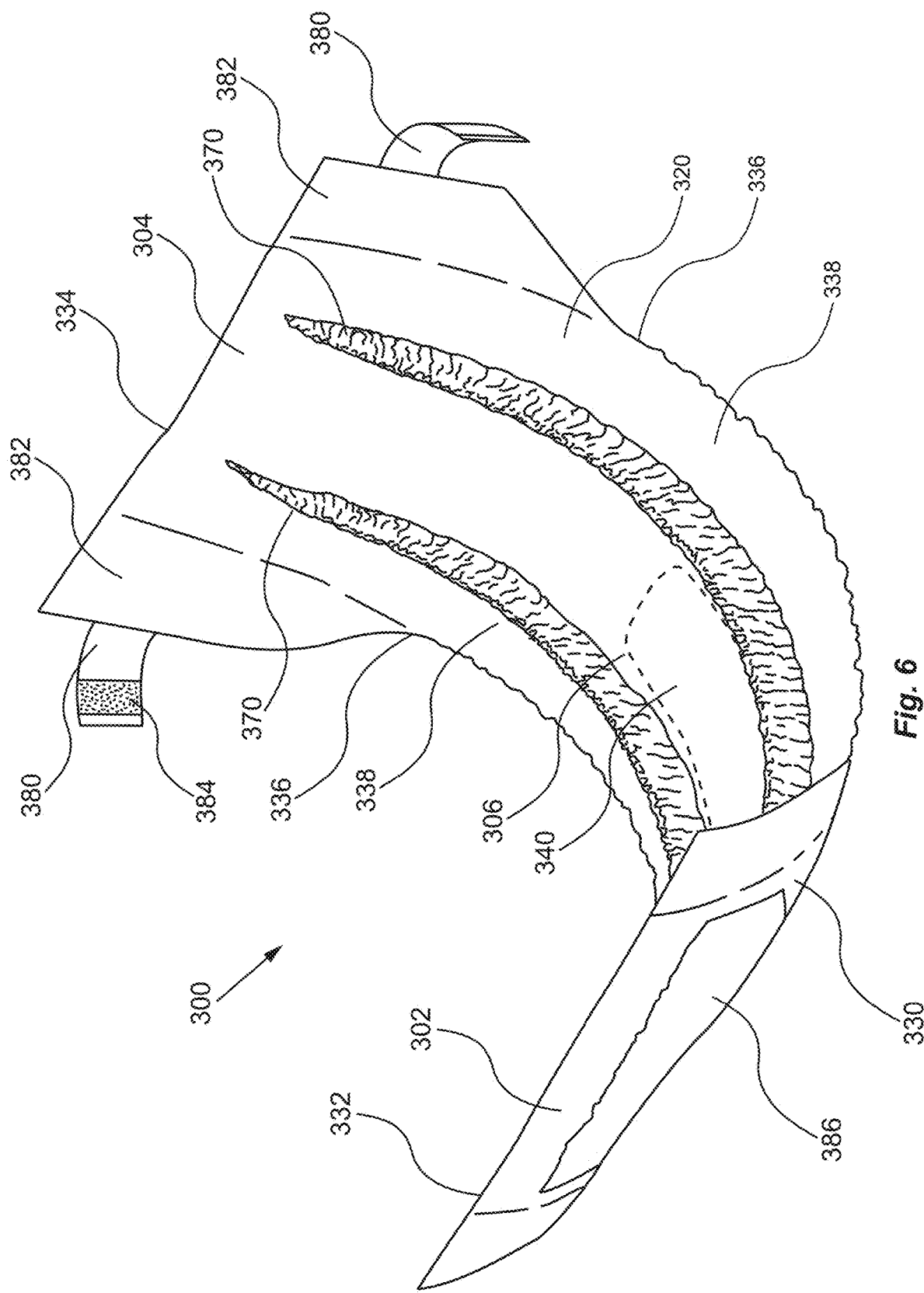
FIG. 6 is an isometric view of a diaper as another embodiment of the present disclosure.

An alternate diaper of the present disclosure is exemplarily shown in FIG. 6. The diaper 300 typically includes a chassis including a front waist portion 302, a back waist portion 304, and a crotch portion 306. The diaper 300 can include a body-side liner or top sheet 320, a liquid absorbent structure or core 340, and an outer cover or bottom sheet 330.

The top sheet 320, absorbent core 340, and bottom sheet 330 may be formed of a material for forming top sheets, absorbent cores, and/or bottom sheets as disclosed herein.

The top sheet 320 is typically arranged to face toward the body of the user, when the diaper is in place and the bottom sheet 330 typically faces away from the user, with the absorbent core 340 interposed therebetween. The top sheet 320 and/or bottom sheet 330 can have a desired shape and dimension.

The bottom sheet 330 can include front edge 332, a back edge 334, and a pair of side edges 336. Each side edge includes a central cut-out to define a respective leg cut out. The crotch portion 306 of the diaper is typically located between the leg cut-outs.

The top sheet 320 may be of the same shape as the bottom sheet 330 or of a different shape and is typically secured to the bottom sheet 330 around peripheral regions thereof, with the absorbent material core 340 interposed therebetween. The bottom sheet and top sheet can be joined together, such as by an adhesive, which can be applied by any one or more of spraying, slot-coat extrusion, and printing. The applied adhesive can be in any desired configuration or pattern, such as in the form of any of continuous beads, discontinuous beads, continuous swirls, discontinuous swirls, meltblown patterns, and spray patterns. Alternatively, the joining of layers and structures of the absorbent article can be accomplished by, for example, heat sealing or ultrasonic bonding. The absorbent core may also be adhered to the bottom sheet or top sheet as described above.

Each lateral side edge 336 of the diaper 300 can be rendered elastic by utilizing plural, e.g., three, longitudinally extending elastic material, e.g., 620 decitex LYCRA® spandex threads or strands 338 disposed along the length of the cut away portion of that side edge. The strands may be attained from E.I. DuPont de Nemours and Company, Wilmington, Del., and are typically secured to the absorbent article by an elastic adhesive, such as that used to hold the elastic foam of the waist portion in place. Further, the elastic adhesive can be intermittently applied along the top sheet to allow the diaper to be stretchable along the leg cut-outs and not all the way to the edges of the respective waist portions, thereby allowing the diaper to closely conform around the legs of the wearer for impeding the egress of waste material from the crotch region. Other arrangements can be used to elasticize the sides of the crotch portion of the diaper. For example, instead of plural longitudinally extending elastic threads 338, multiple strands of elastic material can be arranged in other orientations, such as in intersecting, diagonal, or any combination of orientations. In other cases, a film or laminate of elastomeric material can be utilized to provide the desired elastic property.

The bottom sheet 330 or cover may be formed of a laminated sheet of a non-woven material and film (with the non-woven side positioned as the outermost layer). Such material should be hydrophobic, soft in texture, and strong in tensile strength. For example, one particular material is a spunbond-meltblown-spunbond (SMS) web. The spunbond layer may be made of polypropylene fibers. Such composites can advantageously serve as a liquid barrier while providing a soft, arm outer fabric texture. The non-woven outer cover can also be made of cloth-like materials, e.g., spun-bond or thermal-bond non-woven web made of polypropylene, polyethylene, polyester, bi-component fibers such as polyethylene/polypropylene or polyethylene/polyester, or any combinations of these fibers. Various multiple layer configurations or fiber denier variations may be used.

Other materials that may be used to form the bottom sheet 330 include, for example, polypropylene films, co-extruded films (polyethylene and ethylene vinyl acetate), co-polymer films (polyethylene/polypropylene), and polylaminates (polypropylene nonwoven and polyethylene film). The material may be selected or constructed to allow water vapor to pass through, while being impervious to liquid water. The water vapor transmission rate of this layer may be from about 200 to about 4000 $g/m^2$ over a 24-hour period.

In order to enable urine to quickly and efficiently pass through the top sheet for subsequent transference to the absorbent core 340 for trapping therein, the top sheet 320 is preferably liquid permeable. The top sheet may be of textile-like films and fabrics. The top sheet can be made of non-woven materials that are pervious to liquid, soft and pliable. The non-woven material can be spun-bonded polypropylene; spun-bonded polyethylene; carded thermally bonded webs of staple fibers such as polypropylene, polyester, polyethylene; and/or sheath/core bi-component fibers having a core of polyester or polypropylene and a sheath of polyethylene. In other advantageous cases, for example, the top sheet can be of fusible fiber pulp or air laid composite, which may include cellulose fiber and/or binders in addition to thermoplastic fibers, or hydroentangled non-woven composites.

In other configurations, the top sheet 320 may be formed of a liquid impermeable material having a plurality of apertures or pores extending therethrough which provides selectively tailorable liquid permeability characteristics by, for example, selecting the size, density, and/or distribution of the apertures.

The absorbent core 340 is as described above. The core can be of any shape and can be a single, integral absorbent structure, or can include a plurality of individual separate absorbent structures and/or absorbent materials that are operably assembled together.

The diaper 300 can also include a pair of conventional "standing leg gathers" or cuffs 370 or liquid-impervious gaskets to provide leakage control in the crotch region. The standing leg gathers are typically located so that they extend along the leg opening region of the diaper. Each standing leg gather can be elasticized and can extend from the edge of the front waist portion to the edge of the rear waist portion and along respective side marginal edges of the core 340 and upstanding from the top sheet 320. The standing leg gathers can be secured in place by an adhesive, e.g., construction adhesive.

The diaper 300 can be held in place on the body of the wearer by, for example, a pair of fastening tabs or tapes 380 projecting outward from a pair of respective ear portions 382 forming the side edges of the top sheet 320 of the diaper contiguous with the back waist portion 334. Each tab 380 can include a patch 384 of small hooks on its underside surface. Each patch can be arranged to be releasably secured to a "landing zone" portion 386 on the back sheet 330 in the front waist region of the diaper. The landing zone can be located at a position so that when the diaper is folded in half with the front waist portion disposed opposite the back waist portion, the landing zone 386 will be aligned with the tabs 380.

The landing zone 386 generally includes a rectangular panel possessing an outer surface having a myriad of small loops arranged to be engaged by the small hooks of the patch 384 of each fastening tab.

If desired, the core 340 may be held in place by a hydrophilic construction adhesive, such as CYCLOFLEX® adhesive from National Starch and Chemical Corporation, Bridgewater, N.J. In such an arrangement, the adhesive may be applied on the internal surface of top sheet 320 and/or back sheet 330.

The size and shape of the various pockets can be selected to accommodate volumetric expansion of the absorbent materials therein during absorption process. For example, the permeable inner layer can be pleated or have a wrinkled surface to maintain the contour when the superabsorbent polymer expands upon absorption. In other cases, the permeable inner layer can also be made of expandable or elastic fibrous material to accommodate expansion during absorption.

Having described the present disclosure in detail, it will be apparent that modifications and variations are possible without departing from the scope of the present disclosure defined in the appended claims. For example, different types of superabsorbent material can be used to tailor the performance characteristics of the absorbent core or the absorbent article, at various relative amounts and at various regions of the core or the absorbent article.

When introducing elements of the present disclosure or the embodiments(s) thereof, the articles "a", "an", "the" and "said" are intended to mean that there are one or more of the elements. The terms "comprising", "including" and "having" are intended to be inclusive and mean that there may be additional elements other than the listed elements. While the above description refers to many devices, methods, and/or elements as including or having certain features and/or components, it is to be understood that disclosure also encompasses devices, methods, and/or elements "consisting essentially of" or "consisting of" those features and/or components.

Thus, the transitional phrase "consisting of" excludes any element, step, or ingredient not specified in the claim, closing the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole.

The transitional phrase "consisting essentially of" limits the scope of a claim to the specified materials or steps and those that do not materially affect the basic and novel characteristic(s) of the claimed invention.

While the above description contains many specifics, these specifics should not be construed as limitations on the scope of the present disclosure, but merely as exemplifications of embodiments thereof. It is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Those skilled in the art will envision many other possible variations that are within the scope and spirit of the present disclosure.

The invention claimed is:

1. An absorbent article with an absorbent core, the core comprising:
   a first fluid permeable layer;
   a second layer;
   a network of filament portions between the first fluid permeable layer and the second layer, the network of filament portions defining a plurality of apertures extending through the network,
   wherein the filament portions of the network are secured to the first fluid permeable layer and the second layer and define a plurality of pockets in the absorbent core configured to contain a superabsorbent material therewithin; and
   a superabsorbent material contained within the plurality of pockets formed by the fluid permeable layer, the filament portions, and the second layer.

2. The absorbent article of claim 1, wherein the absorbent core further comprises fluff pulp in at least one of the plurality of pockets.

3. The absorbent article of claim 1, wherein the network comprises a polymeric material having a melting point less than a melting point of a material comprising the first fluid permeable layer.

4. The absorbent article of claim 3, wherein the polymeric material comprises a polymer selected from the group consisting of polyethylene, polypropylene, polyester, and polyamide.

5. The absorbent article of claim 1, wherein the plurality of pockets is defined by the filament portions of the network adhesively secured to the first fluid permeable layer and to the second layer.

6. The absorbent article of claim 1, wherein the superabsorbent material comprises starch-graft polymers and cross-linked polyacrylate polymers.

7. The absorbent article of claim 1, wherein the superabsorbent material is a polymer selected from the group consisting of polyacrylamide, polyethylene oxide, polyvinyl alcohol, polysuccinimide, and hydrolyzed polyacrylonitrile.

8. The absorbent article of claim 1, wherein at least a portion of the pockets are sized to have at least one dimension in a range of from about 0.125 inch to about 1 inch.

9. The absorbent article of claim 1 having at least a portion of said plurality of pockets with a first area and at least a portion of said plurality of pockets with a second area, said first area greater than the second area, and wherein said at least a portion of said plurality of pockets with said first area disposed at a peripheral zone of the absorbent article.

10. The absorbent article of claim 1, wherein at least a portion of the filaments comprises an elastomeric material with a diameter in a range of from about 250 microns to about 500 microns.

11. The absorbent article of claim 1, wherein the article is selected from the group consisting of diapers and protective undergarments.

12. The absorbent article of claim 1, wherein the superabsorbent material is contained within at least one pocket of the plurality of pockets.

13. The absorbent article of claim 12, wherein the superabsorbent material is contained within each pocket of the plurality of pockets.

14. The absorbent article of claim 1, wherein the second layer is substantially coextensive with the first fluid permeable layer.

15. The absorbent article of claim 1, wherein the second layer is opposed to the first fluid permeable layer.

16. An absorbent article comprising:
a first layer;
a a second layer;
a network of filament portions between the first layer and the second layer, the filament portions defining a plurality of apertures extending through the network,
wherein the filament portions of the network—secured to the first layer and the second layer define a plurality of pockets in the article, the plurality of pockets configured to contain superabsorbent material within respective apertures in the network and between the first layer and the second layer; and
a superabsorbent material contained within the plurality of pockets formed by the first layer, the filament portions, and the second layer.

17. The absorbent article of claim 16, wherein the plurality of pockets is defined by the filament portions of the network adhesively secured to the top sheet first layer and to the second layer.

18. The absorbent article of claim 16, wherein the superabsorbent material is contained within at least one pocket of the plurality of pockets.

19. The absorbent article of claim 18, wherein the superabsorbent material is contained within each pocket of the plurality of pockets.

20. The absorbent article of claim 1, wherein the filament portions are formed via ultrasonic bonding.

21. The absorbent article of claim 1, wherein the first fluid permeable layer, the filament portions and the second layer comprise polypropylene.

22. The absorbent article of claim 1, wherein the second layer is an impermeable outer layer.

23. The absorbent article of claim 16, wherein the filament portions are formed via ultrasonic bonding.

24. The absorbent article of claim 16, wherein the first layer, the filament portions and the second layer comprise polypropylene.

25. The absorbent article of claim 16, wherein the second layer is an impermeable outer layer.

* * * * *